United States Patent
Breton et al.

(10) Patent No.: US 10,456,429 B2
(45) Date of Patent: Oct. 29, 2019

(54) USE OF PROBIOTIC MICRO-ORGANISMS AS AN AGENT THAT PROMOTES THE SYNTHESIS OF MELANIN

(71) Applicants: L'OREAL, Paris (FR); NESTEC S.A., Vevey (CH)

(72) Inventors: Lionel Breton, Versailles (FR); Audrey Gueniche, Rueil-Malmaison (FR); Michela Zuccolo, Paris (FR); Annick Mercenier, Bussigny (CH); Guénolé Prioult, Lausanne (CH)

(73) Assignees: L'OREAL, Paris (FR); NESTEC S.A., Vevey (CH)

( * ) Notice: Subject to any disclaimer, the term of this patent is extended or adjusted under 35 U.S.C. 154(b) by 130 days.

(21) Appl. No.: 14/654,166

(22) PCT Filed: Dec. 18, 2013

(86) PCT No.: PCT/EP2013/077206
§ 371 (c)(1),
(2) Date: Jun. 19, 2015

(87) PCT Pub. No.: WO2014/096078
PCT Pub. Date: Jun. 26, 2014

(65) Prior Publication Data
US 2015/0343002 A1  Dec. 3, 2015

(30) Foreign Application Priority Data
Dec. 21, 2012  (FR) .................... 12 62706

(51) Int. Cl.
| *A61K 35/745* | (2015.01) |
| *A61Q 19/04* | (2006.01) |
| *A61K 8/99* | (2017.01) |
| *A61Q 5/10* | (2006.01) |

(52) U.S. Cl.
CPC .............. *A61K 35/745* (2013.01); *A61K 8/99* (2013.01); *A61Q 19/04* (2013.01); *A61Q 5/10* (2013.01)

(58) Field of Classification Search
None
See application file for complete search history.

(56) References Cited

U.S. PATENT DOCUMENTS

| 7,183,101 B2 * | 2/2007 | Arigoni | ................ A23C 9/1234 |
| | | | 435/252.1 |
| 8,802,077 B2 * | 8/2014 | Petit | ...................... A23L 33/135 |
| | | | 424/93.4 |
| 2010/0272699 A1 | 10/2010 | Pain et al. | |
| 2011/0268743 A1 | 11/2011 | Benyacoub et al. | |

FOREIGN PATENT DOCUMENTS

| EP | 2138186 A1 | 12/2009 |
| FR | 2916977 A1 | 12/2008 |
| FR | 2920306 A1 | 3/2009 |
| WO | WO 2009/053564 | * 4/2009 |
| WO | WO 2010/130663 | * 11/2010 |

OTHER PUBLICATIONS

Makino et al. "Transmission of Intestinal *Bifidobacterium longum* subsp. *longum* Strains from Mother to Infant, Determined by Multilocus Sequencing Typing and Amplified Fragment Length Polymorphism" Applied and Environmental Microbiology, Oct. 2011, p. 6788-6793 vol. 77, No. 19.*
English Translation for WO 2009/053564, 62 pages.*
Lin et al. "In Vitro and in Vivo Melanogenesis Inhibition by Biochanin A from Trifolium pratense" Biosci. Biotechnol. Biochem., 75 (5), 914-918, 2011 (Year: 2011).*
Kameyama et al. "Inhibitory effect of magnesium L-ascorbyl-2-phosphate (VC-PMG) on melanogenesis in vitro and in vivo" Journal of the American Academy of Dermatology Jan. 1996, pp. 29-33 (Year: 1996).*
Shimogaki et al. "In vitro and in vivo evaluation of ellagic acid on melanogenesis inhibition" International Journal of Cosmetic Science, 22 291-303 (2000) (Year: 2000).*
Choi et al. "Effects of vitamin C vs. multivitamin on melanogenesis: comparative study in vitro and in vivo" International Journal of Dermatology 2010, 49, 218-226 (Year: 2010).*
Schell et al. "The genome sequence of Bifidobacterium longum reflects its adaptation to the human gastrointestinal tract" PNAS Oct. 29, 2002, vol. 99, No. 22, pp. 14422-14427 (Year: 2002).*
Gueimonde et al. "Bile-Inducible Efflux Transporter from Bifidobacterium longum NCC2705, Conferring Bile Resistance" Applied and Environmental Microbiology, May 2009, p. 3153-3160 (Year: 2009).*
Yuan et al. "Analysis of Host-Inducing Proteome Changes in Bifidobacterium longum NCC2705 Grown in Vivo" Journal of Proteome Research 2008, 7, 375-385 (Year: 2008).*
Parche et al. "Lactose-over-Glucose Preference in Bifidobacterium longum NCC2705: glcP, Encoding a Glucose Transporter, Is Subject to Lactose Repression" Journal of Bacteriology, Feb. 2006, p. 1260-1265 (Year: 2006).*

* cited by examiner

*Primary Examiner* — Thane Underdahl
(74) *Attorney, Agent, or Firm* — Polsinelli PC (57) ABSTRACT

The present invention relates to the topical use of *Bifidobacterium longum* subsp. *longum* CNCM I-2618, as a pro-pigmenting agent, in particular in the prevention and/or treatment of alterations of skin and/or hair color homogeneity and for creating a uniform complexion.

11 Claims, 1 Drawing Sheet

USE OF PROBIOTIC MICRO-ORGANISMS AS AN AGENT THAT PROMOTES THE SYNTHESIS OF MELANIN

CROSS REFERENCE TO RELATED APPLICATIONS

This application is a National Phase filing under 35 U.S.C. § 371 of PCT/EP2013/077206 filed on Dec. 18, 2013; and this application claims priority to Application No. 1262706 filed in France on Dec. 21, 2012. The entire contents of each application are hereby incorporated by reference.

The present invention relates to the topical use of the *Bifidobacterium longum* strain registered under number I-2618 with CNCM to induce pigmentation of the skin and hair, and homogenize the complexion.

Human hair and skin color is dependent on various factors, such as the seasons of the year, ethnic origin, gender and age. It is essentially determined by the concentration and distribution, in keratinocytes, of melanin produced by melanocytes. Melanin, a natural pigment recognized for the antiradical and sun ray-absorbing properties thereof, is a physiological protective agent of the skin, existing in two main forms: eumelanin and pheomelanin.

Melanocytes are specialized cells that synthesize melanin and distribute same to keratinocytes via specific organelles, melanosomes.

In the epidermis, the melanocyte is involved in the epidermal melanin unit, forming a distribution network between melanocytes and keratinocytes, consisting of a melanocyte surrounded by approximately 36 adjacent keratinocytes. Melanocytes account for approximately 5 to 10% of the cells of the basal layer of the epidermis. All individuals, regardless of phototype, have approximately the same number of melanocytes for a given skin area. The differences in pigmentation between individuals are not due to the number of melanocytes, but to the nature of the melanin synthesized and the biochemical and functional properties of the melanosomes.

Melanosomes are highly specialized organelles whose sole function is the synthesis and transfer of melanin. They emerge from the endoplasmic reticulum in the form of spherical vacuoles called pre-melanosomes which contain an amorphous protein substrate, but no melanogenic enzymes. As the pre-melanosome matures, the amorphous substrate is organized into a fibrillar structure oriented in the longitudinal axis of the melanosome. A distinction is made between four stages of melanosome development corresponding to the intensity of melanization. Melanin is deposited uniformly on the internal fibrillar network of the melanosome and the opacity of the organelle increases to saturation. As melanin synthesis is carried out in the melanosomes, the latter move from the perinuclear region to the dendritic tip of the melanocytes. By phagocytosis, the dendritic tip is captured by the keratinocytes, the membranes are degraded and the melanin content of the melanosomes is redistributed in the keratinocytes. Melanin is thus distributed in the epidermis, ensuring the tanning and protection thereof.

With regard to the color of hair and body hair, this is particularly based on the presence in variable quantities and ratios of two groups of melanins: eumelanins (brown to black pigments) and pheomelanins (red to yellow pigments). The pigmentation of hair and body hair requires the presence of melanocytes at the hair follicle bulb. The hair follicle is a tubular invagination of the epidermis penetrating to the deep layers of the dermis. The inner part of the bulb is a zone of cell proliferation containing the precursors of the keratinized cells forming the hair. The melanocytes at the hair follicle bulb are in an active state, i.e. they synthesize melanin. These pigments are transmitted to the keratinocytes intended to form the hair shaft, giving rise to the growth of a pigmented hair or body hair.

The mechanisms leading to pigmentation of skin and keratin fibers, particularly body hair and hair, are highly regulated mechanisms, dependent on multiple hormonal or cellular factors.

Melanocyte homeostasis, finely regulated by these hormonal or cellular factors, helps give the skin and keratin fibers a homogeneous natural pigmentation of varying intensity, creating an attractive aesthetic and cosmetic appearance.

However, in most populations, obtaining a brown skin color and maintaining a constant hair color are important aspirations. Maintaining a tanned complexion or naturally pigmented hair are factors playing a strong role in obtaining an attractive cosmetic appearance.

Moreover, modifications of the physiology of the epidermis and the hair follicle, particularly associated with age, may alter the pigmentation of the skin and hair and body hair. In particular, these modifications may be conveyed by melanocyte homeostasis dysregulation, indicated by proliferation, maturation or survival disorders, possibly accompanied by a melanogenesis anomaly or imbalance.

Furthermore, pigmentation diseases exist such as for example vitiligo which is an autoimmune disease characterized by the appearance of white patches on the skin associated with a pigmentation deficiency.

Therefore, there is a genuine need for a product facilitating and/or enhancing pigmentation of the skin and/or body hair and/or hair, and suitable for topical use.

Numerous solutions have been proposed in the field of artificial coloring by supplying exogenous colorants, such as DHA, supposed to give the skin and/or body hair and/or hair a color as close as possible to the natural color or, in the field of natural coloring, by stimulating the natural pigmentation processes, for example by using agents stimulating melanogenesis with or without UV action.

It has thus been proposed to use compositions containing a phosphodiesterase inhibitor (WO 95/17161), prostaglandins (WO 95/11003), DNA fragments (WO 95/01773), DNA coding for MSH receptors (WO 94/04674), diacylglycerols (WO 94/04122), tyrosine derivatives (EP 0585018), black horehound extracts (WO 93/10804), or xanthine extracts (WO 91/07945). These various compounds act, directly or indirectly via α-MSH or prostaglandins, so as to stimulate melanin biosynthesis, with or without the action of UV.

Excellent results have indeed been obtained with the solutions proposed in the prior art, but the compounds used frequently have non-negligible side-effects or are complex mixtures with no specificity.

The discovery of alternative substances having an effect on pigmentation of the skin and/or body hair and/or hair thus remains a major research objective.

In particular, there is still a need to provide alternative agents, particularly cosmetics, preferably suitable for topical administration, physiologically inducing pigmentation.

There is still a need to provide alternative agents promoting melanogenesis.

There is still a need to provide alternative agents for regulating the synthesis or accumulation of melanin in the epidermis.

There is still a need to provide alternative agents for increasing melanin deposits in hair and/or body hair.

There is still a need to provide alternative agents for facilitating and/or enhancing pigmentation of the skin and/or body hair and/or hair in the field of dermatology and cosmetics.

There is still a need to provide alternative agents suitable for use for preventing and/or limiting and/or stopping the development of canities, or maintaining the natural pigmentation of gray or white hair and/or body hair.

The aim of the invention is particularly to meet these needs.

Probiotic micro-organisms, micro-organisms suitable for having a positive effect on health of the subject ingesting same, are widely used in the field of cosmetics.

As such, the application FR 2 756 181 describes the use of cosmetic compositions based on the inactivated culture of *Bifidobacterium* type bacteria, mint oil and an acid to remove pigment spots.

The application EP 1 110 555 describes the use of a bacterial agent, for example a *Bifidobacterium* bacterial extract, for stabilizing and/or regenerating the skin ecosystem of mammals and treating, inter alia, *pityriasis versicolor*.

The application FR 2 912 917 describes the use of a conditioned culture medium, obtained by contact with peripheral blood cells stimulated by probiotics, for treating signs of inflammation and/or immunity disorders, such as inflammatory hyperpigmentation, vitiligo or canities.

The application WO 2008/015343 describes the use of yeast extracts for increasing melanin synthesis, and treating vitiligo and canities.

The application WO 2007/073122 describes the use of a rice bran fermented with a lactic bacteria for whitening the skin by preventing melanin synthesis.

The application US 2002/0168388 describes the use of compositions comprising inactivated bacteria and a plant extracellular matrix extract for countering damage caused by UV rays.

The application WO 02/28402 describes the use of compositions comprising probiotics for balancing the immune function of the skin after exposure to stress conditions.

The application FR 2 834 718 describes the use of active substances obtained by fermenting plant or fruit seeds with *Lactobacillus, Lactococcus* or *Leuconostoc* bacteria for protecting the skin from the harmful effects of UV rays and regulating melanogenesis in the skin and hair.

The application FR 2 920 307 describes the use of probiotics for treating signs of discomfort and/or skin signs associated with a surface skin treatment, including skin whitening.

The application FR 2 920 306 describes the use of a *Bifidobacterium* lysate for preventing a diminishing of and/or reinforcing the skin barrier function, and thus preventing and/or reducing skin irritations or signs of skin aging.

The application FR 2 920 300 describes the use of hesperidin in conjunction with a probiotic for reinforcing the skin barrier function and thus treating the skin signs of aging.

The use of the probiotic *Bifidobacterium* as a pro-pigmenting agent has however not been suggested.

However, the inventors have demonstrated herein, surprisingly, that the bacterial strain *Bifidobacterium longum* subsp. *longum* registered on Jan. 29, 2001 under the number I-2618 with CNCM (Paris, France) according to the Budapest Treaty, made it possible to induce skin or hair pigmentation significantly. In particular, the specific probiotic strain makes it possible to induce more pigmentation that other known types of probiotics such as the *Propionibacterium freudenreichii* or *Bacillus coagulans* strains, but also other *Bifidobacterium longum* strains.

The present invention thus relates to the non-therapeutic cosmetic use of at least one probiotic *Bifidobacterium longum* subsp. *longum* micro-organism strain registered on Jan. 29, 2001 under the number I-2618 with CNCM (Paris, France) according to the Budapest Treaty, as an agent inducing skin and/or hair pigmentation, for homogenizing the color of the skin and/or hair, particularly for preventing and/or treating an alteration of skin and/or hair color homogeneity of pathological origin, said at least one probiotic *Bifidobacterium longum* subsp. *longum* CNCM I-2618 micro-organism strain being administered topically.

It also relates to a probiotic *Bifidobacterium longum* subsp. *longum* micro-organism strain registered on Jan. 29, 2001 under the number I-2618 with CNCM (Paris, France) according to the Budapest Treaty, for use, as an agent inducing skin and/or hair pigmentation, for preventing and/or treating an alteration of skin and/or hair color homogeneity of pathological origin, said *Bifidobacterium longum* subsp. *longum* CNCM I-2618 micro-organism strain being administered topically.

DETAILED DESCRIPTION OF THE INVENTION

*Bifidobacterium longum* subsp. *longum* CNCM I-2618

The *Bifidobacterium longum* bacteria strain used within the scope of the present invention is a probiotic micro-organism.

The term "probiotic micro-organism" denotes live micro-organisms, which when consumed in adequate amounts, confer a health effect on the host ("*Joint FAO/WHO Expert Consultation on Evaluation of Health and Nutritional Properties of Probiotic in Food Including Powder Milk with Live Lactic Acid Bacteria*, Oct. 6, 2001").

In the sense of the present invention, the micro-organism envisaged may be used live, or inactivated, incapable of replicating. A fraction thereof or one of the components of this micro-organism may also be used.

The *Bifidobacterium longum* subsp. *longum* strain used within the scope of the invention was registered on Jan. 29, 2001 with CNCM (Paris, France), under the number I-2618, and is for example described in Schell et al. (2002) *Proc. Nat. Acad. Sci. USA* 99:14422-14427. The sequence of the genome thereof is referenced under the GenBank number AE014295.

In the context of the invention, the GenBank references cited above are those available on Jul. 3, 2012.

According to one alternative embodiment of the invention, the probiotic *Bifidobacterium longum* subsp. *longum* CNCM I-2618 micro-organism used within the scope of the invention may be used in isolated or purified form, i.e. not mixed with one or more compound(s) liable to be associated therewith in the original medium thereof or in the propagation medium thereof.

According to one alternative embodiment of the invention, the probiotic *Bifidobacterium longum* subsp. *longum* CNCM I-2618 micro-organism used within the scope of the invention may be used in a live, semi-active, inactivated or dead form.

In particular, the probiotic *Bifidobacterium longum* subsp. *longum* CNCM I-2618 micro-organism used within the scope of the invention may be used in a live or inactivated form.

According to one advantageous embodiment of the invention, the probiotic *Bifidobacterium longum* subsp. *longum* CNCM I-2618 micro-organism may be used in inactivated or dead form.

In the sense of the invention, an "inactivated" micro-organism is a micro-organism which is no longer capable, temporarily or definitively, of forming colonies in culture.

In the sense of the invention, a "dead" micro-organism is a micro-organism which is no longer capable, definitively, of forming colonies in culture.

The dead or inactivated micro-organisms may have intact or ruptured cell membranes. As such, the term "inactivated" also denotes the micro-organism extracts and lysates as detailed hereinafter. Dead or inactivated micro-organisms may be obtained by any method known to those skilled in the art.

According to one advantageous embodiment, the probiotic *Bifidobacterium longum* subsp. *longum* CNCM I-2618 micro-organisms used according to the invention are at least partially inactivated or dead.

The term "at least partially inactivated probiotic *Bifidobacterium longum* subsp. *longum* CNCM I-2618 micro-organisms" denotes a preparation of probiotic *Bifidobacterium longum* subsp. *longum* CNCM I-2618 micro-organisms according to the invention comprising at 80%, particularly at least 85%, more particularly at least 90%, or at least 95%, at least 99%, or at least 99.99% inactivated probiotic *Bifidobacterium longum* subsp. *longum* CNCM I-2618 micro-organisms expressed in colony-forming units (cfu) relative to all of the non-inactivated live probiotic *Bifidobacterium longum* subsp. *longum* CNCM I-2618 micro-organisms contained in the initial preparation before undergoing an inactivation process. The inactivation rate obtained is dependent on the application conditions of the inactivation method which are adjusted by those skilled in the art according to the inactivation rate to be obtained. According to one embodiment, the invention includes the use of a preparation comprising a maximum number, preferably 100%, of inactivated probiotic *Bifidobacterium longum* subsp. *longum* CNCM I-2618 micro-organisms.

An inactivated probiotic *Bifidobacterium longum* subsp. *longum* CNCM I-2618 micro-organism suitable for the invention may be prepared by irradiation, heat treatment or, under certain conditions, by freeze-drying a preparation of probiotic *Bifidobacterium longum* subsp. *longum* CNCM I-2618 micro-organism. These methods are known to those skilled in the art. Further known techniques including high-pressure treatment or extrusion may also be envisaged by those skilled in the art.

More particularly, the inactivation of probiotic micro-organisms by irradiation may include the use of gamma rays, X-rays or UV exposure. The type of radiation, intensity, dose and exposure time are adjusted by those skilled in the art according to the quantity and nature of the probiotic *Bifidobacterium longum* subsp. *longum* CNCM I-2618 micro-organisms to be inactivated.

Thermal inactivation may be carried out by incubating the probiotic *Bifidobacterium longum* subsp. *longum* CNCM I-2618 micro-organisms according to the invention for a given period of time, for example from 10 s to 90 min at a temperature of 100 to 150° C. According to the micro-organism to be inactivated, a longer treatment, for example 2 hours, at 170° C. may be envisaged.

Thermal inactivation may also be performed by autoclaving by subjecting the probiotic *Bifidobacterium longum* subsp. *longum* CNCM I-2618 micro-organisms according to the invention to a temperature of 121° C., for at least 20 minutes and to an atmospheric pressure of 2 bar.

Alternatively, thermal inactivation may be performed by subjecting the probiotic *Bifidobacterium longum* subsp. *longum* CNCM I-2618 micro-organisms to a series of freezing-thawing cycles.

Freeze-drying inactivation may be performed using any method known in the field. Advantageously, probiotic *Bifidobacterium longum* subsp. *longum* CNCM I-2618 micro-organisms inactivated by freeze-drying may be replaced in culture.

Preferably, a probiotic *Bifidobacterium longum* subsp. *longum* CNCM I-2618 micro-organism suitable for the invention is used in an inactivated form obtained by irradiation, particularly by gamma irradiation.

An inactivated probiotic *Bifidobacterium longum* subsp. *longum* CNCM I-2618 micro-organism according to the invention may be used in whole form, i.e. essentially in the native form thereof, or in the form of extracts or lysates comprising fractions and/or metabolites of this micro-organism.

In the sense of the invention, the term "fraction" denotes a fragment or component of said micro-organism endowed with efficacy for inducing melanin synthesis by analogy with said whole micro-organism.

In the sense of the invention, the term "metabolite" denotes any substance derived from the metabolism of the micro-organisms, and particularly secreted by the *Bifidobacterium longum* subsp. *longum* CNCM I-2618 micro-organisms in question according to the invention and also endowed with efficacy for inducing melanin synthesis.

In the sense of the invention, the term "extract" denotes a preparation containing inactivated micro-organisms wherein the cellular structure has not undergone any destruction or dissolution. The biological cells are overall not fragmented.

An extract or a lysate suitable for the invention may be prepared using *Bifidobacterium longum* subsp. *longum* CNCM I-2618 bacteria at the end of the growth phase.

According to one embodiment, a probiotic *Bifidobacterium longum* subsp. *longum* CNCM I-2618 micro-organism suitable for the invention may be prepared in the form of a lysate.

A lysate in the sense of the invention commonly denotes a material obtained following the destruction or dissolution of biological cells by a phenomenon referred to as cell lysis thus inducing the release of the intracellular biological constituents naturally contained in the cells of the micro-organism in question and fragments of cell membrane components. In the sense of the present invention, the term "lysate" is used equally to denote the entire lysate obtained by inactivating the micro-organism in question or merely a fraction thereof. The lysate used is thus formed completely or partially of the intracellular biological constituents and the constituents of the cell walls and membranes of the probiotic *Bifidobacterium longum* subsp. *longum* CNCM I-2618 micro-organism of interest.

Within the scope of the invention, use may be advantageously made of:
  an extract containing inactivated micro-organisms of the micro-organism strain in question, or
  a lysate obtained by lysis or inactivation of the micro-organism in question.

This cellular inactivation for obtaining an extract or a lysate may be carried out using different technologies, such as for example an osmotic shock, thermal shock, by ultrasound, or under mechanical stress such as centrifugation, or combinations of these different technologies.

More particularly, this lysate may be obtained according to the technology described in the U.S. Pat. No. 4,464,362, and particularly according to the following protocol.

A probiotic micro-organism of interest is cultured anaerobically in a suitable culture medium, for example according to the conditions described in U.S. Pat. No. 4,464,362 and EP 0 043 128. When the stationary phase of development has been reached, the culture medium may be inactivated by pasteurization, for example at a temperature of 60 to 65° C. for 30 min. The micro-organisms may then be collected using a conventional separation technique, for example membrane filtration, centrifuged and optionally resuspended in a sterile NaCl solution at a physiological concentration. In the case of a lysate, this lysate may then be obtained by ultrasound disintegration of such a medium so as to release the cytoplasmic fractions, the cell wall fragments and certain products derived from the metabolism of these micro-organisms. Then all the components in the natural distribution thereof may be stabilized in a weakly acidic aqueous solution.

It is thus possible to obtain a lysate having a concentration in the region of 0.1 to 50%, particularly 1 to 20% and especially approximately 5% by weight of active substance(s) relative to the total weight thereof.

According to one possible alternative to the technology described above, centrifugation may be applied at the end of fermentation (at the start of the stationary phase) prior to heat treatment It may also be envisaged to retrieve the micro-organisms and the supernatant and carry out the heat treatment later, the whole then being suitable for being dried.

Preferably, a *Bifidobacterium longum* subsp. *longum* CNCM I-2618 extract or lysate used within the scope of the invention is obtained by thermal shock. Typically, when the stationary phase of the development of *Bifidobacterium longum* subsp. *longum* CNCM I-2618 is reached, the culture medium containing the micro-organisms may be centrifuged. The micro-organism concentrate may then be inactivated by heat treatment, for example at temperatures of 71.7° C. to 147° C. for 3 s up to several minutes. The bacterial concentration typically contains a portion of the metabolites produced during growth and the bacterial walls subjected to heat treatment. The solution typically has a concentration in the region of 10 to 55%, particularly 12 to 20% and especially approximately 15% by weight of active substance(s) relative to the total weight thereof. The heat treatment applied may be performed directly (direct contact between the product and the heat source such as steam) or indirectly (the product and the heat source are separated by a physical barrier). In the case of direct heat treatment, the treatment times may be shorter, in the region of a few seconds (1 to 15 s). The culture medium containing the micro-organisms (before or after centrifugation) may be concentrated by evaporation. The heat treatment may be applied before and/or after the evaporation step.

The extract or lysate may be used in various forms, such as in the form of a solution or in a powder form, preferably in the form of a solution. Storage in liquid form may require the application of a stabilization treatment such as an ultra-high-temperature (UHT) treatment. Any liquid stabilization method known to those skilled in the art may be envisaged for the solution or suspension of *Bifidobacterium longum* subsp. *longum* CNCM I-2618 micro-organism.

An inactivated probiotic *Bifidobacterium longum* subsp. *longum* CNCM I-2618 micro-organism used with the scope of the invention may be formulated in a composition at a rate of at least 0.0001% expressed in dry weight, particularly at a rate of 0.0001 to 20% and more particularly at a rate of 0.001 to 15%, in particular 0.01 to 10%, and especially 0.1 to 2% relative to the total dry weight of the composition containing same.

A probiotic *Bifidobacterium longum* subsp. *longum* CNCM I-2618 micro-organism used within the scope of the invention is particularly formulated in a composition intended for topical administration.

As a general rule, a composition for topical application according to the invention may generally comprise from $10^3$ to $10^{12}$ cfu/g, particularly from $10^5$ to $10^{10}$ cfu/g and more particularly from $10^7$ to $10^9$ cfu/g of *Bifidobacterium longum* subsp. *longum* CNCM I-2618 micro-organisms per gram of substrate or at equivalent doses calculated for inactivated or dead *Bifidobacterium longum* subsp. *longum* CNCM I-2618 micro-organisms or for fractions of *Bifidobacterium longum* subsp. *longum* CNCM I-2618 micro-organisms or for metabolites produced.

It may be advantageous to use *Bifidobacterium longum* subsp. *longum* CNCM I-2618 micro-organisms in inactivated, or dead, form, particularly presented in the form of a cell extract or lysate, typically containing cell fragments and metabolites.

A *Bifidobacterium longum* subsp. *longum* CNCM I-2618 micro-organism may also be included in a composition in the form of cell component fractions or in the form of metabolites, particularly in the form of an extract or in the form of a lysate. The *Bifidobacterium longum* subsp. *longum* CNCM I-2618 micro-organism(s), metabolite(s) or fraction(s) may also be introduced in the form of a freeze-dried powder, culture supernatant and/or if applicable in a concentrated form.

When a composition comprises metabolites, the metabolite contents in the compositions correspond substantially to the contents liable to be produced by the equivalent of $10^3$ to $10^{15}$ cfu, particularly $10^5$ to $10^{15}$ cfu, and more particularly $10^7$ to $10^{12}$ cfu of live *Bifidobacterium longum* subsp. *longum* CNCM I-2618 micro-organisms per gram of substrate.

The expression of the quantity of metabolites or fractions of a micro-organism in "cfu", or of dead micro-organisms is intended to denote the quantity of this micro-organism required to produce said quantity of metabolites or fractions of micro-organisms.

Cosmetic Composition

In one particular embodiment of the invention, said at least one *Bifidobacterium longum* subsp. *longum* CNCM I-2618 strain, as defined in the section "*Bifidobacterium longum* subsp. *longum* CNCM I-2618" above, is formulated in a cosmetic composition further comprising a cosmetically acceptable vehicle.

The term "cosmetically acceptable vehicle" denotes herein a medium having no unpleasant odor or appearance, and not giving rise to stinging, tautness or redness unacceptable for the user, during the administration thereof, particularly during the topical application thereof on the skin and skin appendages.

The cosmetically acceptable vehicle will be suitable for the topical administration route of the composition, particularly for the nature of the substrate whereon the composition is to be applied, and for the form wherein the composition is intended to be packaged, notably solid or fluid at ambient temperature and atmospheric pressure.

The cosmetic composition used within the scope of the invention may be presented in any dosage forms normally used for the topical mode of administration.

A composition intended for topical administration may be an aqueous, hydroalcoholic or oil solution, a solution or dispersion such as a lotion or serum, an emulsion of liquid or semi-liquid consistency such as a cream, obtained by dispersing a fatty phase in an aqueous phase (O/W) or conversely (W/O), a suspension or an emulsion, of soft, semi-solid or solid consistency, such as a cream or aqueous or anhydrous gel, a multiple emulsion (W/O/W or O/W/O), a microemulsion, a nano-emulsion, a microcapsule preparation, a microparticle preparation, or an ionic and/or non-ionic vesicular dispersion, or a wax/aqueous phase dispersion.

It may also be presented in the form of a transdermal system suitable for active or passive release of said agent(s) transdermally, for example such as a patch or gel patch (hydrogel), or by injection.

These compositions are prepared according to routine methods.

A cosmetic composition used within the scope of the invention may form a composition for the treatment or care of the skin or hair, keratin fibers such as hair, eyelashes or eyebrows, or a sun protection or artificial tanning composition, or a product cleansing or removing makeup from the skin, hair, eyebrows or eyelashes, a deodorant product or a perfuming compound. Preferably, the cosmetic composition used within the scope of the invention is a sun protection or artificial tanning composition.

Such a composition may then be non-colored or slightly colored, and may optionally contain additional cosmetic agents, particularly as stated hereinafter. It may then be used as a skin or lip care base, for example in the form of a lip balm, protecting the lips from the cold and/or sun and/or wind, as a day or night facial and/or body skin care cream.

It may also be presented in the form of optionally treating, optionally coloring shampoo, or conditioner.

A cosmetic composition used within the scope of the invention may also be a colored cosmetic composition and particularly a makeup composition for the skin, keratin fibers, particularly the hair or eyelashes, and/or mucosa, in particular such a composition may be a foundation, blusher, rouge or eyeshadow, anti-wrinkle compound in stick form, lipstick or lip gloss, optionally having care or treatment properties. Preferably it may consist of a colored (beige or green) makeup composition for correcting the color of the complexion.

A composition administered topically may particularly be a cleansing, protection, treatment or care cream, a lotion, a gel or a foam for skin or hair care, such as a cleansing or disinfecting lotion, a bath composition or a deodorant composition.

A cosmetic composition used within the scope of the invention may also consist of a solid preparation forming a soap or a cleansing bar.

According to one embodiment of the invention, a cosmetic composition used within the scope of the invention may be advantageously formulated to be administered onto the scalp, hair and eyelashes, and particularly be prepared in the form of a solution, cream, gel, emulsion, foam or in the form of an aerosol composition also containing a pressurized propellant.

According to one embodiment, a topical cosmetic composition used within the scope of the invention may advantageously be formulated in any dosage form suitable for hair care, particularly in the form of a hair care lotion, for example to be applied daily or twice-weekly, a shampoo, particularly anti-dandruff, a conditioner, particularly to be applied weekly or twice-weekly, a detangling product, a cream or a hair gel, a treating lotion, a dye composition (notably based on oxidation) optionally in the form of a coloring shampoo, a restructuring hair lotion, a perming composition, a lotion or a gel against hair loss, an anti-parasitic shampoo, or a treating shampoo, particularly against seborrhea, a scalp care production particularly anti-irritant, anti-aging, restructuring, or activating blood circulation, a liquid or solid soap for cleansing the scalp to be applied daily, a hair styling product, such as a lacquer, a hairsetting product or a styling gel, a treating mask, a cream or a foaming gel for cleansing hair, or a hair mascara to be applied with brush or comb.

According to one embodiment, for application on eyelashes or body hair, a cosmetic composition used within the scope of the invention may be presented in the form of a mascara, optionally pigmented, to be applied with a brush on the eyelashes or on beard or mustache hair.

According to one particular embodiment, a cosmetic composition used within the scope of the invention may be presented in the form of a cream or a hair lotion, a shampoo or a hair conditioner, a hair or eyelash mascara.

When a cosmetic composition used within the scope of the invention is an emulsion, the proportion of the fatty phase may range from 5 to 80% by weight, and preferably from 10 to 50% by weight relative to the total weight of the composition. The oils, emulsifiers and co-emulsifiers used in the composition in emulsion form are chosen from those conventionally used in the cosmetic field.

The emulsifier and the co-emulsifier may be present, in the cosmetic composition, in a proportion ranging from 0.3% to 30% by weight, and preferably from 0.5% to 20% by weight, relative to the total weight of the composition.

When the cosmetic composition used within the scope of the invention is an oily gel or solution, the fatty phase may represent more than 90% of the total weight of the composition.

In a known manner, the dosage forms intended for topical administration may also contain usual additives in the cosmetic field, such as hydrophilic or lipophilic gelling agents, preservatives, antioxidants, solvents, perfumes, bulking agents, filters, odor absorbers and dyes. The quantities of these various additives are conventionally the quantities used in the cosmetic field, for example from 0.01 to 20% of the total weight of the composition.

These additives, depending on their nature, may be introduced into the fatty phase and/or into the aqueous phase.

As fatty substances suitable for use in the cosmetic compositions used within the scope of the invention, mention may be made of mineral oils such as for example hydrogenated polyisobutene and petroleum jelly, plant oils such as for example a liquid shea butter fraction, sunflower and apricot kernel oil, animal oils such as for example perhydrosqualene, synthetic oils particularly Purcellin oil, isopropyl myristate and ethylhexyl palmitate, unsaturated fatty acids and fluorinated oils such as for example perfluoropolyethers. It is also possible to use fatty alcohols, fatty acids such as for example stearic acid and such as for example waxes particularly paraffin, carnauba and beeswax. It is also possible to use silicone compounds such as silicone oils and for example cyclomethicone and dimethicone, silicone waxes, resins and gums.

As emulsifiers suitable for use in the cosmetic compositions used within the scope of the invention, mention may be made for example of glycerol stearate, polysorbate 60, the cetylstearyl alcohol/oxyethylenated cetylstearyl mixtures having 33 moles of ethylene oxide sold under the trade name Sinnowax AO® by HENKEL, the PEG-6/PEG-32/Glycol Stearate mixture sold under the trade name Tefose® 63 by GATTEFOSSE, PPG-3 myristyl ether, silicone emulsifiers such as cetyldimethicone copolyol and sorbitan mono- or tristearate, PEG-40 stearate, oxyethylenated sorbitan monostearate (20OE).

As solvents suitable for use in the cosmetic compositions used within the scope of the invention, mention may be made of lower alcohols, particularly ethanol and isopropanol, propylene glycol.

The cosmetic composition used within the scope of the invention may also advantageously contain a spring and/or mineral water, particularly chosen from Vittel water, waters from the Vichy basin and La Roche Posay water.

As hydrophilic gelling agents, mention may be made of carboxylic polymers such as carbomer, acrylic copolymers such as acrylate/alkylacrylate copolymers, polyacrylamides and particularly the mixture of polyacrylamide, C13-14 Isoparaffin and Laureth-7 sold under the name Sepigel 305® by SEPPIC, polysaccharides such as cellulose derivatives such as hydroxyalkylcelluloses and particularly hydroxypropylcellulose and hydroxyethylcellulose, natural gums such as guar, carob and xanthan and clays.

As lipophilic gelling agents, mention may be made of modified clays such as bentones, fatty acid metal salts such as aluminum stearates and hydrophobic silica, or ethylcellulose and polyethylene.

In one particularly preferred embodiment of the invention, the cosmetic composition as defined above further comprises an additional cosmetic agent.

Advantageously, such an additional agent may be intended to apply a cosmetic, care or hygiene effect on the skin, hair, eyelashes, body hair and/or scalp.

The additional agents are chosen by those skilled in the art such that they do not impede the effect of the probiotic *Bifidobacterium longum* subsp. *longum* CNCM I-2618 micro-organisms according to the invention.

According to one alternative embodiment, a probiotic *Bifidobacterium longum* subsp. *longum* CNCM I-2618 micro-organism as defined in the section "*Bifidobacterium longum* subsp. *longum* CNCM I-2618", may be advantageously used with, as an additional agent, a non-probiotic micro-organism, particularly the *Vitreoscilla filiformis* strain.

Such a non-probiotic micro-organism may be used in live, semi-active, inactivated or dead form, particularly as defined in the section "*Bifidobacterium longum* subsp. *longum* CNCM I-2618" above. In particular, a *Vitreoscilla filiformis* type micro-organism, as described particularly in the patent application FR 0 625 782, may be used in a live form or in fractionated or whole lysate form with the culture medium thereof after evapo-concentration of the composition in $H_2O$.

The cosmetic composition used within the scope of the invention may further comprise any routine cosmetic additives such as water, solvents, oils, waxes, pigments, bulking agents, surfactants, cosmetic agents, UV filters, polymers, gelling agents, preservatives and perfumes. Obviously, those skilled in the art will take care to choose these optional additional compounds, and/or the quantity thereof, such that the advantageous properties of the active constituents of the composition according to the invention are not, or are substantially not, altered by the envisaged addition. Preferably, the cosmetic composition used within the scope of the invention further comprises UV filters.

Non-therapeutic Cosmetic Use

Surprisingly, the inventors observed that applying probiotic *Bifidobacterium longum* subsp. *longum* CNCM I-2618 type micro-organisms regulates melanocyte homeostasis, by promoting melanin synthesis, more effectively than other probiotic micro-organisms such as *Propionibacterium freudenreichii* or *Bacillus coagulans*, or other *Bifidobacterium longum* strains. As such, the natural pigmentation of the skin, hair and body hair is reinforced thereby. The skin or hair pigmentation obtained in this way is advantageously homogeneous.

The present invention relates more particularly to the non-therapeutic cosmetic use of a *Bifidobacterium longum* subsp. *longum* CNCM I-2618 strain, as defined in the section "*Bifidobacterium longum* subsp. *longum* CNCM I-2618" above, optionally formulated in a cosmetic composition as defined in the section "Cosmetic composition" above, as an agent inducing skin and/or hair pigmentation, for physiologically inducing pigmentation and thus in particular preventing and/or treating an alteration of skin and/or hair color homogeneity, said probiotic *Bifidobacterium longum* subsp. *longum* CNCM I-2618 micro-organism strain being administered topically.

The cosmetic composition used within the scope of the invention may particularly be used in healthy subjects, typically subjects not exhibiting alterations of skin and/or hair color homogeneity of pathological origin.

It may, particularly in healthy subjects, be used as a tanning agent, advantageously as a tanning agent independent of sunlight and/or UV rays, or to accelerate and/or intensify tanning.

It may also, particularly in healthy subjects, be used to render the complexion and/or the color of the complexion more uniform.

The cosmetic composition used within the scope of the invention may also be used for preventing and/or cosmetically treating a skin and/or hair pigmentation defect resulting from a melanocyte homeostasis imbalance.

The melanocyte homeostasis imbalance may be a melanocyte proliferation and/or maturation and/or survival imbalance.

Proliferation, maturation and survival relate to the different stages of life of a cell of a tissue of an organism, i.e. the division thereof from a stem cell or a parent cell, the differentiation thereof enabling the acquisition thereby of characteristics specific to the tissue wherein it is placed, such as for example the expression of the various enzymes and proteins required for melanogenesis, and the maintenance thereof until the senescence thereof and apoptosis. Dysregulation of these stages may result in an imbalance in respect of melanocyte distribution in the epidermis or follicle, or an imbalance in respect of melanogenesis affecting for example the natural color of the epidermis, hair or body hair.

In one particular embodiment, the pigmentation defects concerned by the invention result from a melanogenesis imbalance.

The melanocyte homeostasis imbalance resulting in the pigmentation defects concerned by the invention may also be associated with skin and scalp aging, and particularly be worsened by this aging.

The pigmentation disorders concerned by the invention may relate to the epidermis, scalp, hair, body hair or eyelashes.

As cosmetic hair pigmentation defects addressed by the invention, mention may particularly be made of canities.

Canities is a natural whitening of the hair that appears with age, and is essentially associated with a decrease in melanin in the hair shaft. More specifically, canities is linked with a specific and progressive rarefaction of hair melanocytes, affecting both the bulb melanocytes and the melanocyte precursor cells. Advantageously, using the invention makes it possible to reduce or even impede or delay the appearance of gray hairs and graying of hair. Advantageously, the present invention makes it possible to stimulate, or even reactivate, melanogenesis, so as to delay, reduce, or decrease canities.

The composition used within the scope of the invention may also be used in subjects exhibiting alterations of skin and/or hair color homogeneity, particularly subjects exhibiting cosmetic skin and/or hair pigmentation defects associated with an accumulation, particularly heterogeneous, of melanin, for homogenizing the color of the skin and/or hair.

Such skin and/or hair pigmentation defects associated with heterogeneous melanin accumulation include melasma, acne pigmentation effects, post-inflammatory pigmentation, depigmentation caused by burns or surgery and benign facial dyschromia.

In these applications, the compositions used within the scope of the invention make it possible to lessen the dyschromia observed and homogenize the color of the skin, particularly by increasing or enhancing skin pigmentation around hyperpigmented areas and/or by increasing or enhancing skin pigmentation at hypopigmented areas.

Preferably, the alteration of skin and/or hair color homogeneity addressed by the present invention is selected in the group consisting of canities, melasma, acne pigmentation effects, post-inflammatory pigmentation, depigmentation caused by burns or surgery and benign facial dyschromia.

The present invention also relates to a non-therapeutic cosmetic treatment method for physiologically inducing pigmentation of the skin and/or hair, and thus homogenizing the color of the skin and/or hair, and particularly preventing and/or treating an alteration of skin and/or hair color homogeneity, wherein a subject is administered topically a cosmetically effective quantity of a *Bifidobacterium longum* subsp. *longum* CNCM I-2618 strain, as defined in the section "*Bifidobacterium longum* subsp. *longum* CNCM I-2618" above, optionally formulated in a cosmetic composition as defined in the section "Cosmetic composition" above.

The term "cosmetically effective quantity" denotes herein a sufficient quantity of the agents used within the scope of the invention in order to treat and/or prevent said cosmetic disorder, which does not induce unacceptable side-effects for the user.

This *Bifidobacterium longum* subsp. *longum* CNCM I-2618 strain, optionally formulated in a cosmetic composition, is administered topically.

Advantageously, the cosmetic composition is applied for example in the form of a mask, on the skin, scalp or hair.

The *Bifidobacterium longum* subsp. *longum* CNCM I-2618 strain, optionally formulated in a cosmetic composition, used within the scope of the invention may particularly be applied on the face or on the body.

Therapeutic Applications

The present invention also relates to a method for preventing and/or treating an alteration of skin and/or hair color homogeneity of pathological origin in a subject, including the topical administration to a subject requiring same of a therapeutically effective quantity of a probiotic *Bifidobacterium longum* subsp. *longum* CNCM I-2618 strain as defined in the section "*Bifidobacterium longum* subsp. *longum* CNCM I-2618" above.

The present invention also relates to the use of a *Bifidobacterium longum* subsp. *longum* CNCM I-2618 strain as defined in the section "*Bifidobacterium longum* subsp. *longum* CNCM I-2618" above, for the production of a pharmaceutical composition, suitable for topical administration, for preventing and/or treating an alteration of skin and/or hair color homogeneity of pathological origin.

As used within the scope of the embodiments of the invention associated with therapeutic use of the probiotic *Bifidobacterium longum* subsp. *longum* CNCM I-2618 micro-organisms defined in the section "*Bifidobacterium longum* subsp. *longum* CNCM I-2618" above, the term "alteration of skin and/or hair color homogeneity of pathological origin" refers to an alteration of skin and/or hair color homogeneity observed with dermatological conditions, resulting from a deficiency or lack of melanin or heterogeneous melanin distribution, particularly dyspigmentation.

The term "dyspigmentation" denotes an anomaly of pathological origin in the formation or distribution of melanin in the skin or hair.

Skin and/or hair pigmentation diseases differ from the cosmetic scope by the degree of severity and intensity of the symptoms whereby they are manifested.

In the case of alterations resulting from a deficiency or lack of melanin, the probiotic *Bifidobacterium longum* subsp. *longum* CNCM I-2618 micro-organisms defined above will make it possible to homogenize the color of the skin, particularly by increasing and/or enhancing skin pigmentation in depigmented or hypopigmented areas.

Such alterations particularly include alterations of skin color homogeneity associated with vitiligo.

In the case of alterations resulting from excess melanin, the probiotic *Bifidobacterium longum* subsp. *longum* CNCM I-2618 micro-organisms defined above will make it possible to homogenize the color of the skin, particularly by increasing and/or enhancing skin pigmentation around hyperpigmented areas.

Such alterations particularly include alterations of skin or complexion color homogeneity associated, inter alia, with actinic lentigo or meadow grass dermatitis.

According to one embodiment, the alterations of skin and/or hair color homogeneity of pathological origin are chosen from actinic lentigo, meadow grass dermatitis and vitilgo In the description and in the examples hereinafter, unless specified otherwise, the percentages are percentages by weight and the value ranges worded as "between . . . and . . . " include the upper and lower limits specified.

The ingredients are mixed, prior to the packaging thereof, in order and under conditions readily determined by those skilled in the art.

The content and the nature of the ingredients used in the compositions according to the invention are adjusted by those skilled in the art so as not to substantially affect the required properties for the compositions according to the invention.

The examples hereinafter are given by way of illustration and are not intended to restrict the field of the invention.

EXAMPLES

Example 1

Induction of Melanin Synthesis by *Bifidobacterium longum* Subsp. *longum* CNCM I-2618

Figure 1:
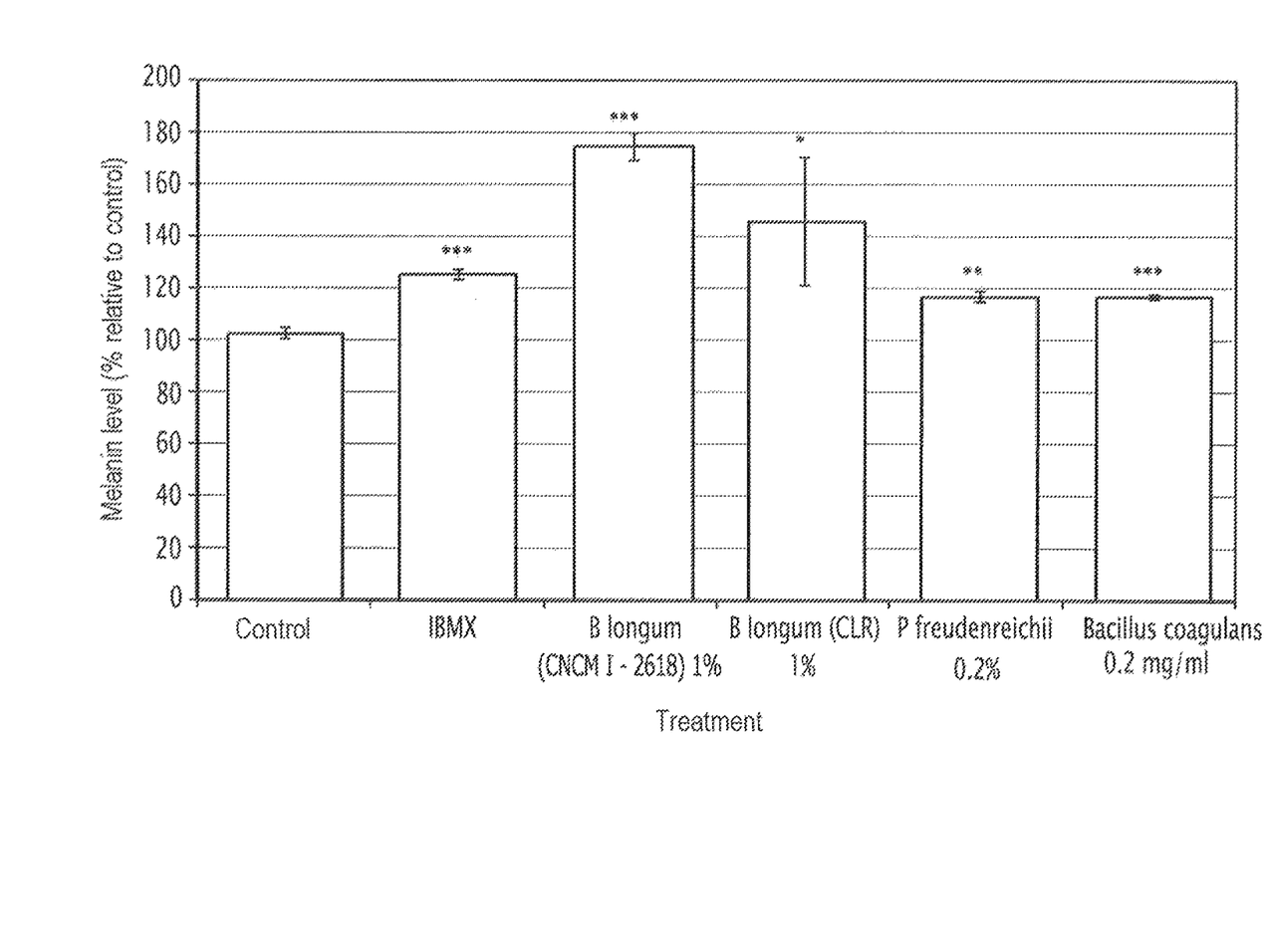
The FIGURE is a set of bar graphs showing the level of melanin, as a percentage relative to the control, quantified in primary keratinocyte (NHEK) and primary melanocyte (NHEM) co-cultures incubated for 72 hours with a culture medium only (control), 200 μM IBMX (IBMX) as the positive control, a *Bifidobacterium longum* subsp. *longum* CNCM I-2618 lysate or extract (*B. longum* CNCM I-2618 1%), a *Bifidobacterium longum* Repair Complex CLR® lysate (*B. longum* CLR 1%), a *Propionibacterium freudenreichii* lysate (*P. freudenreichii* 0.2%) and a *Bacillus coagulans* lysate (*B. coagulans* 0.2 mg/ml).

This example demonstrates the pro-pigmenting activity of the probiotic *Bifidobacterium longum* subsp. *longum* CNCM I-2618 micro-organism.
Materials and Methods
Human primary melanocytes (NHEM) were inoculated in 24-well plates in the presence (co-culture) of normal human epidermal keratinocytes (NHEK) and cultured for 24 hours. The cells were then treated with nothing (negative control), IBMX (positive control, 200 μM), a *Bifidobacterium longum* subsp. *longum* CNCM I-2618 lysate or extract (1%), a comparative lysate of another *Bifidobacterium longum* strain (Repair Complex CLR® 1%), a *Propionibacterium freudenreichii* extract (0.2%) or a *Bacillus coagulans* extract (2 mg/ml).
After treatment, the cells were incubated for 72 hours, all the experimental conditions having been created in triplicate. After 72 hours of incubation, the cells were lyzed with a 0.5 M NaOH solution so as to extract the melanin. The optical density of the samples was measured at 405 nm, with reference to an exogenous melanin range (standard melanin curve 0.39 to 100 μg/ml).
The results are expressed as a relative stimulation percentage in relation to the control cultured in standard co-culture medium. They were analyzed with Student's statistical test:
\*: $0.01 < p \leq 0.05$ significant;
\*\*: $0.001 < p \leq 0.01$ very significant;
\*\*\*: $p < 0.001$ extremely significant
Results
The inventors thus demonstrated that incubating NHEK/NHEM co-cultures with probiotic micro-organism lysates made it possible to significantly increase melanin production by melanocytes relative to untreated co-cultures (see FIGURE).
They further demonstrated, surprisingly, that the specific use of *Bifidobacterium longum* subsp. *longum* CNCM I-2618 strain lysates or extracts made it possible to increase melanin production even further relative to the use of other probiotics such as *P. freudenreichii* or *B. coagulans* and even relative to lysates of other *Bifidobacterium longum* strains. Indeed, incubating NHEK/NHEM co-cultures with *B. longum* subsp. *longum* CNCM I-2618 lysates induces an increase of melanin production of approximately 1.7-fold relative to an untreated control, whereas *P. freudenreichii* and *B. coagulans* lysates only make it possible to attain an increase of approximately 1.1-fold and the *B. longum* Repair Complex CLR® lysate an increase of approximately 1.4-fold. It should be noted that the increase observed with *B. longum* subsp. *longum* CNCM I-2618 is even greater than that obtained with the positive control IBMX.

As such, these results demonstrate that the probiotic *Bifidobacterium longum* subsp. *longum* CNCM I-2618 micro-organism may be used very effectively as a pro-pigmenting agent.

Example 2

Topical Compositions According to the Invention

This example describes compositions intended for topical use that are particularly suitable for the use of the present invention.

Unless specified otherwise, the values hereinafter are expressed as a percentage by weight relative to the weight of the composition.

Example 2A

Facial Lotion

| | |
|---|---|
| Freeze-dried powder of *Bifidobacterium longum* subsp. *longum* CNCM I-2618 | 0.50 |
| Magnesium gluconate | 3.00 |
| Calcium lactate | 2.00 |
| Antioxidant | 0.05 |
| Isopropanol | 40.0 |
| Preservative | 0.30 |
| Water | qs 100% |

Example 2B

Face Care Cream (Sleep Restorative)

| | |
|---|---|
| Freeze-dried powder of *Bifidobacterium longum* subsp. *longum* CNCM I-2618 | 1.00 |
| Glycerol stearate | 1.00 |
| Ceylstearyl alcohol/oxyethylenated cetylstearyl alcohol containing 30 moles EO (Sinnowax AO ® sold by HENKEL) | 3.00 |
| Cetyl alcohol | 1.00 |
| Dimethicone (DC 200 Fluid ® sold by DOW CORNING) | 1.00 |
| Petroleum jelly | 6.00 |
| Isopropyl myristate (Estol IMP 1514 ® sold by UNICHEMA) | 3.00 |
| Antioxidant | 0.05 |
| Glycerin | 20.00 |
| Preservative | 0.30 |
| Water | qs 100% |

Example 2C

Face Care Gel (to be Stored at 4° C.)

| | |
|---|---|
| *Bifidobacterium longum* subsp. *longum* CNCM I-2618 | $10^{12}$ cfu |
| Hydroxypropylcellulose (Klucel H ® sold by HERCULES) | 1.00 |
| Vitamin E | 2.50 |
| Antioxidant | 0.05 |
| Isopropanol | 40.00 |
| Preservative | 0.30 |
| Water | qs 100% |

Example 2D

Face Care Gel (to be Stored at 4° C.)

| | |
|---|---|
| Aqueous lysate of *Bifidobacterium longum* subsp. *longum* CNCM I-2618 | 10.00 |
| Hydroxypropylcellulose (Klucel H ® sold by HERCULES) | 1.00 |
| Inactivated and evapo-concentrated whole culture (evapoconcentrate) of *Vitreoscilla filiformis* | 0.30 |
| Vitamin E | 2.50 |
| Antioxidant | 0.05 |
| Isopropanol | 40.00 |
| Preservative | 0.30 |
| Water | qs 100% |

The invention claimed is:

1. A non-therapeutic cosmetic method which comprises topically administering to a subject at least one probiotic *Bifidobacterium longum* subsp. *longum* micro-organism strain registered on Jan. 29, 2001 with CNCM (Paris, France) under the number I-2618, as an agent inducing skin and/or hair pigmentation, for promoting melanin synthesis thereby homogenizing the color of the skin and/or hair of said subject, wherein said *Bifidobacterium longum* subsp. *longum* CNCM I-2618 strain is in at least partially inactivated form and is presented in the form of a cell extract or lysate containing cell fragments and metabolites.

2. The cosmetic method according to claim 1, for preventing and/or treating an alteration of skin and/or hair color homogeneity.

3. The cosmetic method according to claim 2, wherein the alteration of skin and/or hair color homogeneity is selected in the group consisting of canities, melasma, acne pigmentation after-effects, post-inflammatory pigmentation, depigmentation caused by burns or surgery and benign facial dyschromia.

4. The cosmetic method according to claim 1, wherein said *Bifidobacterium longum* subsp. *longum* CNCM I-2618 strain is formulated in a cosmetic composition further comprising a cosmetically acceptable vehicle.

5. The cosmetic method according to claim 4, wherein the cosmetic composition further comprises an additional cosmetic agent.

6. The cosmetic method according to claim 1, wherein the *Bifidobacterium longum* subsp. *longum* CNCM I-2618 micro-organism is inactivated by heat treatment.

7. The cosmetic method according to claim 1, which comprises topically administering to a subject of at least one probiotic *Bifidobacterium longum* subsp. *longum* micro-organism strain registered on Jan. 29, 2001 with CNCM (Paris, France) under the number I-2618, as an agent inducing skin pigmentation, for promoting melanin synthesis thereby homogenizing the color of the skin of said subject,
wherein said *Bifidobacterium longum* subsp. *longum* CNCM I-2618 strain is in at least partially inactivated form and is presented in the form of a cell extract or lysate containing cell fragments and metabolites.

8. A therapeutic method, for preventing and/or treating an alteration of skin and/or hair color homogeneity of pathological origin, comprising administering topically to a subject in need thereof an effective amount of a probiotic *Bifidobacterium longum* subsp. *longum* micro-organism strain registered on Jan. 29, 2001 with CNCM (Paris, France) under the number I-2618, as an agent inducing skin and/or hair pigmentation, for promoting melanin synthesis, wherein said *Bifidobacterium longum* subsp. *longum* CNCM I-2618 strain is in at least partially inactivated form and is presented in the form of a cell extract or lysate containing cell fragments and metabolites.

9. The method according to claim 8, wherein said alteration of skin and/or hair color homogeneity is selected in the group consisting of actinic lentigo, meadow grass dermatitis and vitiligo.

10. The method according to claim 8, wherein said strain is inactivated by heat treatment.

11. The method according to claim 8, for preventing and/or treating an alteration of skin color homogeneity of pathological origin.

* * * * *